US007273000B2

(12) United States Patent
Thiem et al.

(10) Patent No.: US 7,273,000 B2
(45) Date of Patent: Sep. 25, 2007

(54) ROTARY MICROTOME AND COLLECTION ELEMENT FOR A ROTARY MICROTOME

(75) Inventors: Stefan Thiem, Heidelberg (DE); Roland Walter, Neulussheim (DE); Rolf Metzner, Dossenheim (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 250 days.

(21) Appl. No.: 10/823,927

(22) Filed: Apr. 14, 2004

(65) Prior Publication Data

US 2004/0261597 A1 Dec. 30, 2004

(30) Foreign Application Priority Data

Apr. 15, 2003 (DE) ................................. 103 17 406
Jan. 29, 2004 (DE) ..................... 10 2004 004 355

(51) Int. Cl.
*G01N 1/06* (2006.01)
(52) U.S. Cl. ........................... 83/167; 83/703; 83/915.5
(58) Field of Classification Search .................. 83/167, 83/915.5, 703, 707, 733
See application file for complete search history.

(56) References Cited

U.S. PATENT DOCUMENTS 3,225,639 A * 12/1965 Martinelli .................. 83/915.5
D251,259 S * 3/1979 Converse, Jr. ............... 83/167
4,221,146 A * 9/1980 Kindel et al. ................. 83/167
5,551,326 A * 9/1996 Goodman ..................... 83/167
6,651,538 B2 * 11/2003 Tamura et al. ............. 83/915.5
2005/0115373 A1 * 6/2005 Kunkel ...................... 83/915.5

FOREIGN PATENT DOCUMENTS

| DE | 4205257 | 6/1993 |
| DE | 9218995 | * 10/1996 |
| EP | 0937975 | 8/1999 |

* cited by examiner

*Primary Examiner*—Stephen Choi
(74) *Attorney, Agent, or Firm*—Simpson & Simpson, PLLC (57) ABSTRACT

A rotary microtome (1) is disclosed, having a base part (2) on which a microtome housing (4) and a knife holder (6) are arranged. Also provided is a collection element (8) that surrounds the knife holder on three sides, the collection element having a U-shaped base outline. Also provided are several clamping levers that are associated with the knife holder, at least one clamping lever for the knife holder being arranged operably on a first or a second outer side wall (18a, 18b). In addition, the bottom (12) of the collection element (8) has shaped on it an elevation (22) under which a mechanical coupling is guided from the clamping lever (10c) to the knife holder.

25 Claims, 8 Drawing Sheets

ROTARY MICROTOME AND COLLECTION ELEMENT FOR A ROTARY MICROTOME

CROSS REFERENCE TO RELATED APPLICATIONS

This application claims priority of German patent applications 103 17 406.0, filed Apr. 15, 2003 and 10 2004 004 355.8, filed Jan. 29, 2004, which are incorporated by reference herein.

FIELD OF THE INVENTION

The invention concerns a rotary microtome. The invention further concerns a collection element for a rotary microtome.

BACKGROUND OF THE INVENTION

The series HM 340 I and series HM 355 and HM 360 rotary microtome of the Mikrom company encompasses a large-volume section collection pan. The section collection pan possesses a base outline which is substantially wider than the base outline of the rotary microtome. The section collection pan has beveled outer surfaces that serve as armrests for a user. The knife holder comprises a plurality of clamping levers for clamping and adjusting the knife. The plurality of clamping levers arranged on the knife holder is on the one hand disadvantageous because they can become contaminated by excess thin sections during cutting. The section collection pan having the beveled armrests furthermore requires a great deal of installation space on a laboratory bench, which is detrimental to the compact installation necessary in a routine-analysis laboratory.

A further rotary microtome is disclosed in Patent No. DE 42 05 257 C2. The rotary microtome is equipped with a base part on which a microtome housing and a knife holder are arranged. A pan for the reception of thin sections of a thin-section sample is provided, the pan comprising two side parts spaced apart from one another, and a front part joining the side parts, which together form a pan having a U-shaped base area. The pan having the U-shaped base area is adapted to surround the knife holder on three sides, and the side parts terminate externally at least approximately flush with the microtome housing. Although the space necessary for installation of the rotary microtome is thereby reduced to a minimum, the knife holder nevertheless encompasses a plurality of clamping parts that can be contaminated by thin sections upon utilization of the rotary microtome. This entails an increased cleaning outlay for the rotary microtome and for the section collection pan provided on the rotary microtome.

SUMMARY OF THE INVENTION

It is the object of the invention to create a rotary microtome that is easy to clean, and that has a small number of elements that need to be cleaned.

The aforesaid object is achieved by a rotary microtome comprising:
- a base part on which a microtome housing and a knife holder is arranged;
- a collection element which surrounds the knife holder on three sides, wherein the collection element is defined by a bottom, a first and a second inner side wall, a front wall, and a first and a second outer side wall;
- several clamping levers are coupled with the knife holder; wherein at least one clamping lever for the knife holder is arranged operably on the first or second outer side wall; and
- a mechanical coupling is guided under the bottom of the collection element from the clamping lever to the knife holder.

A further object of the invention is to create a collection element for a rotary microtome that is configured in such a way that contaminations of the mechanical elements of a rotary microtome are reduced.

The aforesaid object is achieved by a collection element comprising:
- a knife holder which the collection element surrounds on three sides, wherein the collection element is defined by a bottom, a first and a second inner side wall, and a front wall, as well as a first and a second outer side wall; and
- a mechanical coupling is guided under the bottom of the collection element, wherein the mechanical coupling provides a mechanical connection from at least one clamping lever, arranged on the first or second outer side wall, to the knife holder.

The advantage of the present invention is that at least one clamping lever for the knife holder is arranged on the first or second outer side wall of the collection element in order to collect the wastes or several sections while cutting with the microtome. Shaped into the bottom of the collection element is an elevation under which a mechanical coupling is guided from the clamping lever to the knife holder. This inventive arrangement reduces the number of clamping levers arranged directly on the knife holder, thereby greatly simplifying cleaning of the knife holder, for example when changing samples.

It is further advantageous if the collection element is embodied as a pan having a U-shaped base outline. The first and the second outer side wall are, in this context, joined to one another by means of an outer front wall, so that the pan surrounds the knife holder on three sides.

It is further advantageous that the collection element comprises a first and a second inner side wall, an inner front wall, and a first and a second outer side wall. The collection element is a housing, open on one side, that is closed off by a bottom, the bottom having a bevel opposite the base part of the microtome housing. The collection element is advantageously configured in such a way that the bottom, the first and the second inner side wall, the inner front wall, and the first and the second outer side wall, in each case abut together to form a fillet. As a result of the fillet, no corners are formed in the interior of the collection element in which sections might lodge, thus complicating efficient cleaning of the collection element at a sample change, or cleaning in general.

It is additionally advantageous for the rotary microtome that the knife holder is equipped with a hex socket screw that makes possible unrestricted angular adjustment of a knife support element and thus of the knife provided on the knife support element. The hex socket screw that is provided thus once again reduces the number of clamping levers provided directly on the knife holder; this once again has an advantageous effect on the cleaning properties of the knife holder.

According to the present invention, the collection element is configured in such a way that the first and the second outer side wall do not form steps with the microtome housing. A user thus cannot inadvertently get caught on the step and possibly separate the collection element from the microtome housing. The collection element and the microtome housing possess mutually corresponding elements which coact in order to join the collection element and microtome housing detachably to one another.

Further advantageous embodiments of the invention may be inferred from the dependent claims.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
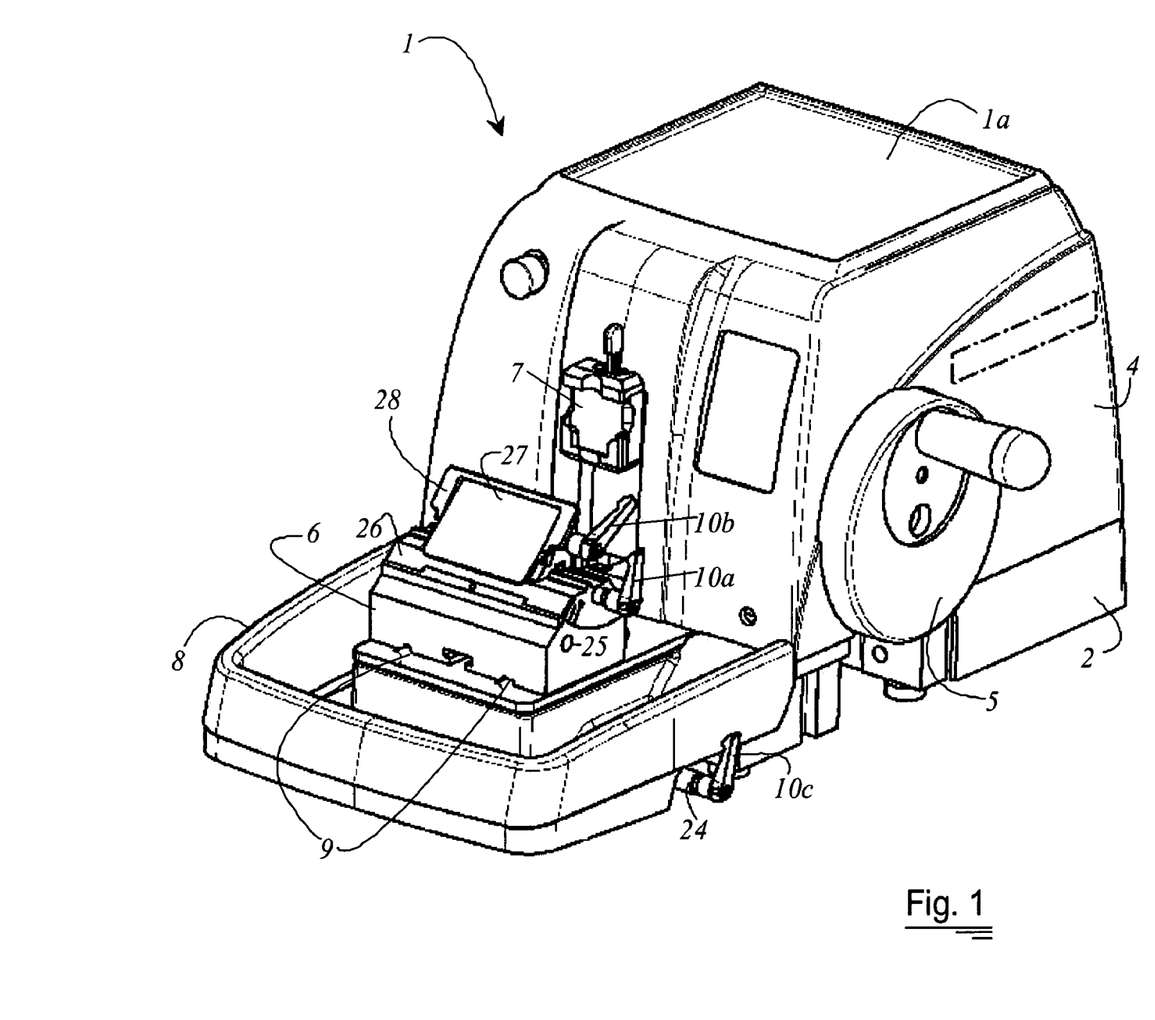
FIG. 1 is a perspective view of the rotary microtome with a pan arranged on the microtome housing.

FIG. 1 is a perspective view of rotary microtome 1. Rotary microtome 1 substantially comprises a base part 2 and a microtome housing 4 provided on the base part. A knife holder 6 is placed on base part 2. Provided opposite knife holder 6 on microtome housing 4 is a sample holder 7 that can be moved up and down by means of a handwheel 5 provided on microtome housing 4. Knife holder 6 and sample holder 7 are arranged oppositely from one another. Provided on base part 2 are two rail elements 9 on which knife holder 6 can be varied in terms of its spacing with respect to sample holder 7. Knife holder 6 is surrounded by a collection element 8. Collection element 8 is U-shaped, and steplessly adjoins microtome housing 4 and base part 2. Arranged on knife holder 6 is a knife support element 26 that can be immobilized by means of a hex socket screw 25. Knife holder 6 has a convexly curved plane that coacts with a concavely curved plane on the knife support element. Knife holder 6 can be moved unrestrictedly on the convexly curved plane of the knife support element, and each angular position is clamped in place using hex socket screw 25. This likewise makes possible unrestricted angular adjustment of a knife 27 provided on knife support element 26. A knife carriage 28 is provided on knife support element 26; and a first clamping lever 10a, mounted on knife support element 26, serves to clamp and immobilize knife carriage 28. A second clamping lever 10b that serves to clamp the knife is provided on knife carriage 28. A third clamping lever 10c is provided on a side wall of collection element 8, and coacts with knife holder 6 via a mechanical coupling 24. Knife holder 6 is clamped with respect to base part 2 by means of third clamping lever 10c.

Figure 2:
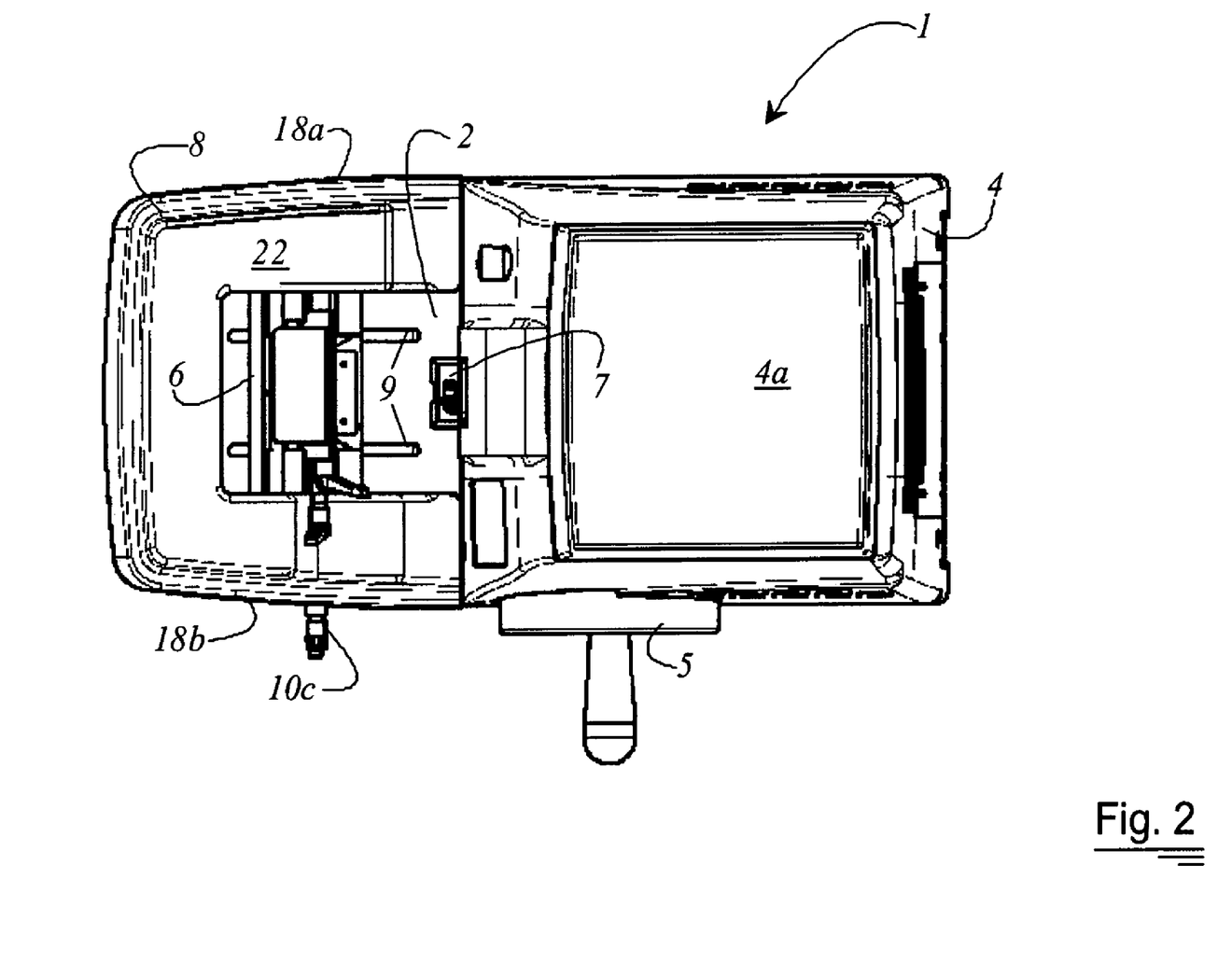
FIG. 2 is a plan view of the rotary microtome with a collection element arranged on the microtome housing to collect cutting waste.

FIG. 2 shows rotary microtome 1 in a plan view. As already mentioned in FIG. 1, knife holder 6 mounted on base part 2 is surrounded by a U-shaped collection element 8. Knife holder 6 can be adjusted on two parallel rail elements 9 in terms of its spacing from sample holder 7. It is also evident from FIG. 2 that collection element 8, at its side wall 18a and side wall 18b, adjoins microtome housing 4 in flush and stepless fashion. The flush adjoining of collection element 8 against microtome housing 4 is particularly advantageous because it makes possible operation of the handwheel without causing the user to bump against a possible step between microtome housing 4 and collection element 8. In order to greatly improve the cleaning properties of the microtome or rotary microtome 1 at a sample change, care has been take to provide a minimal number of clamping elements and operating elements inside collection element 8. For example, knife holder 6 is clamped from outside by way of clamping lever 10c which is provided on a side wall 18b. This has the critical advantage that in the context of a sample change, this clamping lever does not need to be cleaned in order to eliminate contamination residues of other samples in collection element 8 or on knife holder 6. Microtome housing 4 has a deposition surface 4a on which, for example, a user can temporarily place samples.

Figure 3:
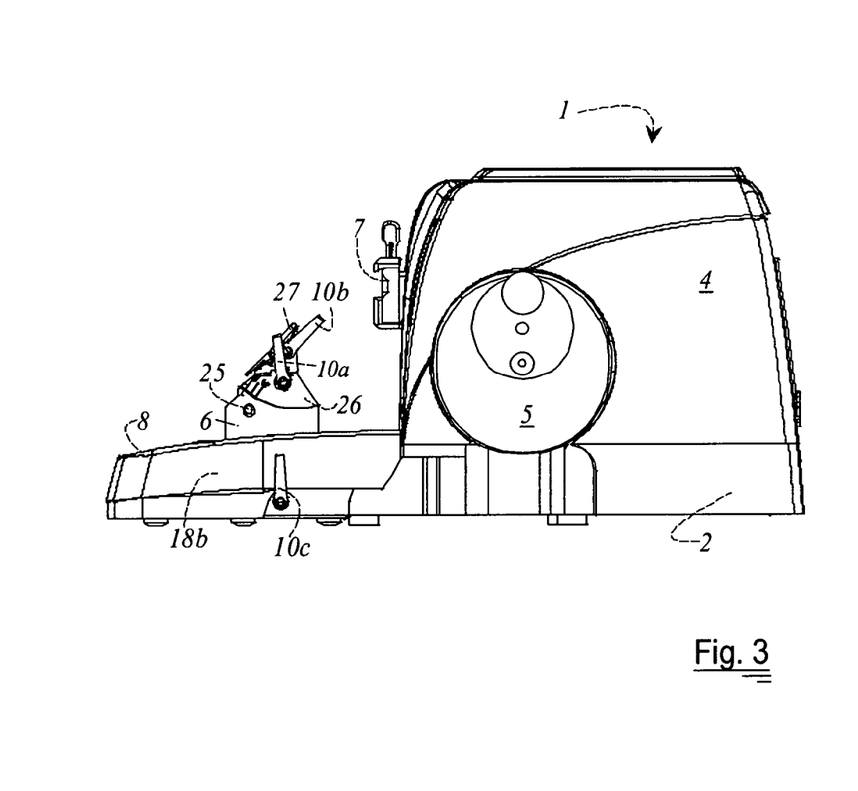
FIG. 3 is a side view of the microtome with a collection element arranged on the microtome housing to collect cutting waste.

FIG. 3 is a side view of rotary microtome 1 according to the present invention. Sample holder 7 is provided in microtome housing 4 opposite knife holder 6. Knife support element 26 is immobilized or clamped in place, in terms of its angular position with respect to knife holder 6, using a hex socket screw 25. First clamping lever 10a serves to clamp knife carriage 28 with respect to knife support element 26. Second knife clamping lever 10b serves to clamp knife 27. Knife holder 6 can be immobilized by means of clamping lever 10c, that clamping lever 10c being provided on an outer side wall 18b of collection element 8.

Figure 4:
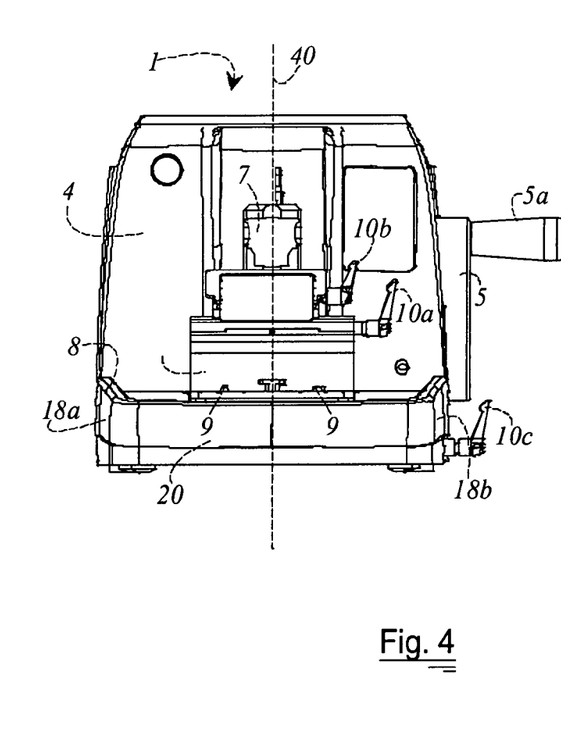
FIG. 4 is a front view of the rotary microtome with a collection element arranged on the microtome housing to collect cutting waste.

FIG. 4 is a front view of rotary microtome 1. As is evident from FIG. 3 and FIG. 4, microtome housing 4 is embodied without corners or edges, thereby considerably facilitating cleaning of the entire microtome housing 4. Knife holder 6 is guided on two parallel rail elements 9 and can be clamped or immobilized by way of third clamping lever 10c, which in this embodiment is provided on outer side wall 18b. The various clamping levers 10a, 10b, and 10c are likewise arranged in such a way that no collisions among clamping levers 10a, 10b, and 10c occur when they are used. Second clamping lever 10b, which is provided for clamping knife 27, is located closest to an axis 40 that approximately represents the center axis of collection element 8 in a front view. First clamping lever 10a follows second clamping lever 10b and is located farther away than second clamping lever 10b from axis 40. Outer side wall 18a, outer side wall 18b, and outer front wall 20 are dimensioned in such a way that first outer side wall 18a and second outer side wall 18b extend toward axis 40. In other words, collection element 8 tapers in the direction of outer front wall 20 that is arranged opposite sample holder 7. This is also particularly advantageous, since a user can assume an ergonomic hand position when operating rotary microtome 1. In addition, a tapering collection element 8 also reduces the space needed for an installation area for rotary microtome 1. The only element projecting beyond the base area of rotary microtome 1 is actuation element 5a provided on handwheel 5.

Figure 5:
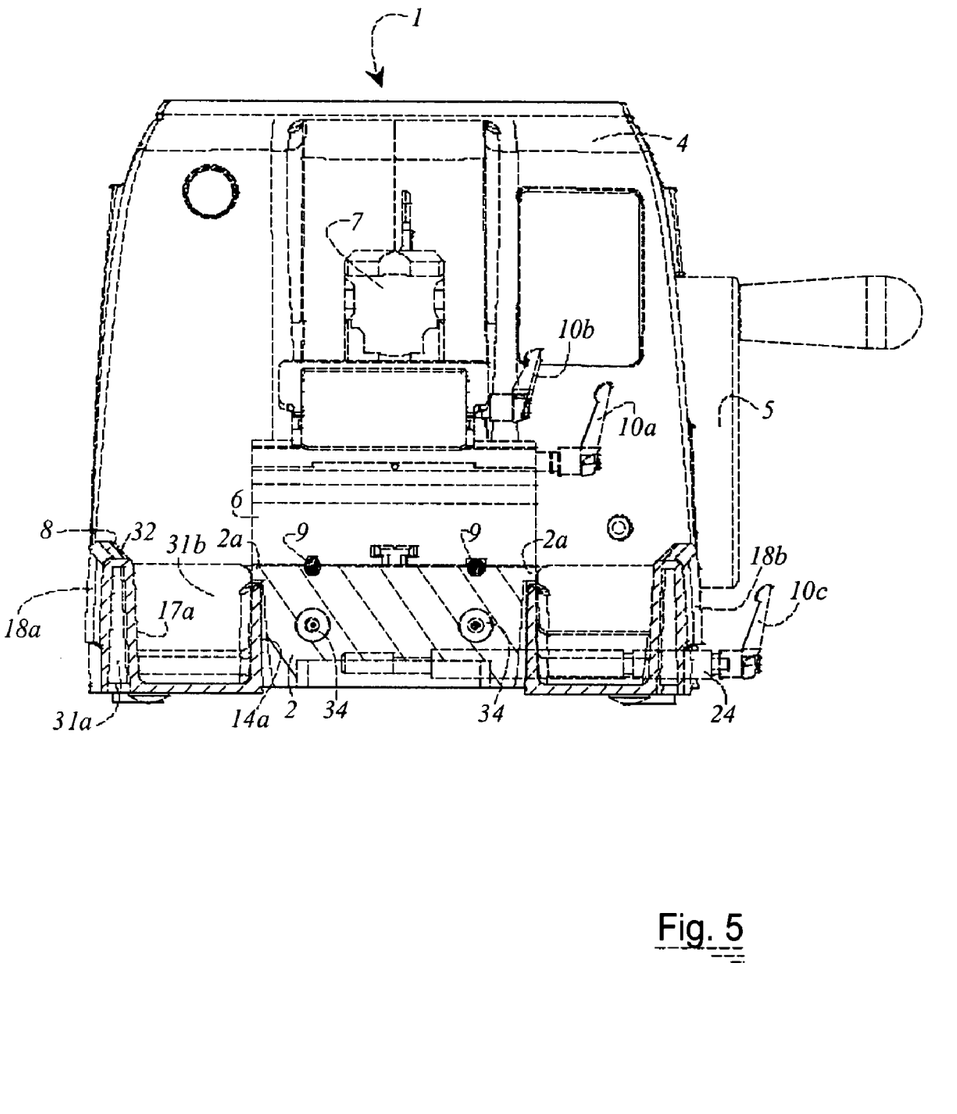
FIG. 5 is a front view of the rotary microtome, the collection element arranged on the microtome housing being partly removed to illustrate the passage of the clamping lever through to the knife holder.

FIG. 5 is a front view of rotary microtome 1 in which portions of collection element 8 are omitted in order to provide a view of the configuration of collection element 8 and the attachment of collection element 8 to base part 2 of rotary microtome 1. Base part 2 has a peripheral step 2a beneath knife holder 6. Peripheral step 2a is dimensioned such that it possesses a width which is greater than or equal to the thickness of first or second inner side wall 14a or 14b and of inner front wall 16. Peripheral step 2a of base part 2 thus ensures that excess sections, or waste in the context of trimming or initial cutting of the sample, fall entirely into collection element 8. As a result, no contamination occurs in any corners or edges of rotary microtome 1. FIG. 5 also shows the physical construction of collection element 8. The cross section through collection element 8 shows clearly that the latter is constructed from a double-U profile. The first part of the double-U profile comprises an outer U 31a and an inner U 31b. Outer U 31a and inner U 31b are arranged rotated 180° with respect to one another. Inner U 31b is made up of inner side wall 14a and inner outer side wall 17a, which are both joined to one another by bottom 12. Outer U 31a is made up of outer inner side wall 17a and outer side wall 18a, which are both joined to one another by a narrow rim 32. The entire collection element 8 is constructed from this profile structure. Base part 2 possesses, on the side located opposite inner front wall 16, at least two magnets 34 that coact with corresponding counterelements on inner front wall 16 (see FIG. 6). Third clamping lever 10c is provided on an outer side wall 18a or 18b; its actuation can be transferred via a mechanical coupling 24 to knife holder 6. Bottom 12 of collection element 8 is embodied in such a way that it covers mechanical coupling 24 and protects it from possible contamination by sample fragments or trimmed fragments during sample preparation.

Figure 6:
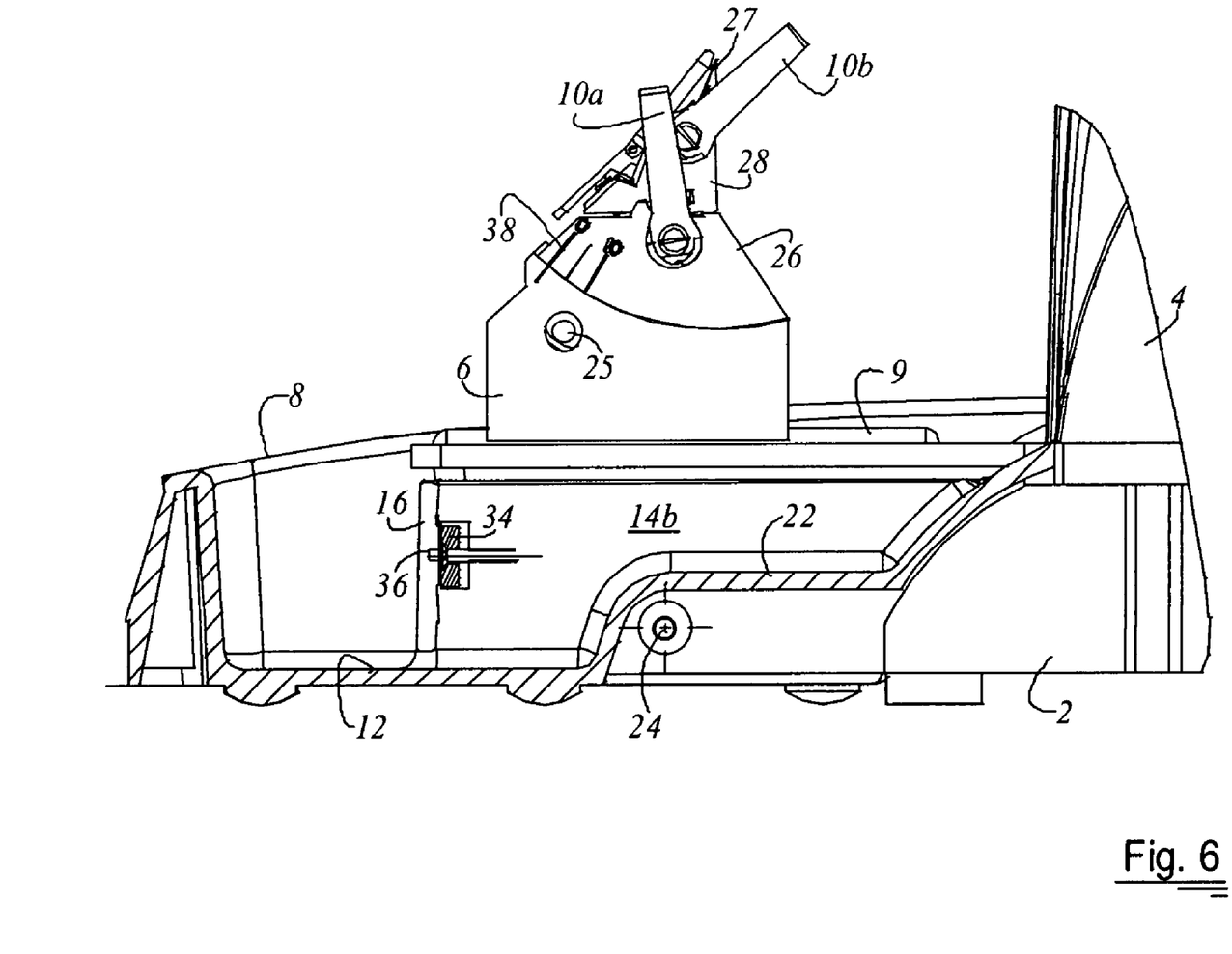
FIG. 6 is an enlarged depiction of the region around the knife holder with portions of the collection element removed, in order to show the coaction of the holding elements between the microtome housing and the collection element for collecting cutting waste.

FIG. 6 is a more detailed view of knife holder 6 and of the arrangement of collection element 8 on base part 2 of microtome housing 4. When collection element 8 is mounted on base part 2 of microtome housing 4, inner front wall 16 abuts against the wall of base part 2 having magnets 34. A magnetic engagement is created by the fact that magnets 34 provided in base part 2 coact with corresponding magnetizable elements 36 mounted in inner front wall 16. In the region of mechanical coupling 24, bottom 12 of collection element 8 is shaped into an elevation 22. Mechanical coupling 24 is guided under elevation 22 and is thus protected from contamination by sample fragments. Provided on knife support element 26 is an angle scale 38 that serves as an indicator of the inclination of knife 27. The inclination of knife 27 can be adjusted by way of knife support element 26, unrestricted adjustment being possible and immobilization of knife support element 26 being achieved by way of hex socket screw 25 arranged on knife holder 6. As already mentioned several times, knife holder 6 is arranged displaceably on rail elements 9. Immobilization of knife holder 6 is accomplished by way of third clamping lever 10c, which coacts via mechanical coupling 24 with knife holder 6.

Figure 7:
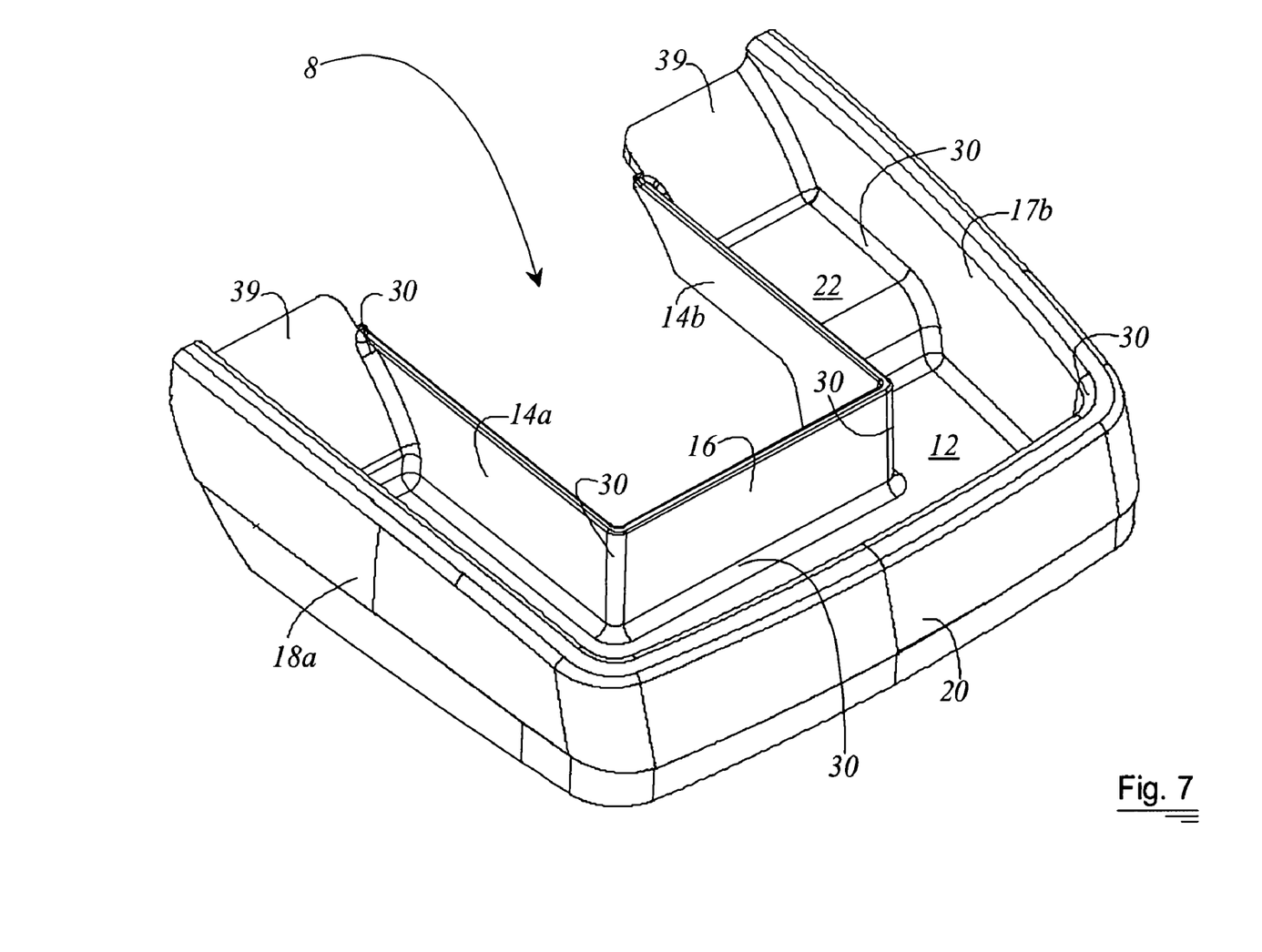
FIG. 7 is a perspective depiction of the pan that can be associated with a microtome housing.

FIG. 7 is a perspective view of collection element 8. As already mentioned several times, collection element 8 is U-shaped. In this embodiment, collection element 8 is constituted substantially from a first inner side wall 14a, an inner front wall 16, and a second inner side wall 14b, joined via a bottom 12 respectively to an outer side wall 18a, an outer front wall 20, and an outer side wall 18b. For simplicity's sake, a description of the double-U-shaped profile of collection element 8 is omitted here. Bottom 12 continues, on the side located opposite outer front wall 20, into a respective contour surface 39 that adapts to a corresponding configuration of base part 2. The transition between bottom 12 and outer side wall 18b or outer side wall 18a or outer front wall 20 is equipped with a fillet 30. A fillet 30 is likewise configured at the transition of bottom 12 to inner side wall 14a, to inner front wall 16, and to inner side wall 14b. A fillet is likewise provided at the locations at which inner side wall 14a encounters front wall 16, or inner side wall 14b encounters front wall 16. Further fillets 30 are provided at the meeting points of outer side wall 18a and outer front wall 20, and of outer side wall 18b and outer front wall 20. Configured in bottom 12 of collection element 8 is an elevation 22 under which, as already described in FIG. 5, mechanical coupling 24 is guided. Collection element 8 is equipped with fillets 30 at all corners and edges. This has the critical advantage that deposits of sample fragments cannot form in either corners or edges. A configuration of collection element 8 with fillets 30 furthermore greatly facilitates cleaning. In addition, the absence of corners and edges considerably reduces the risk of injury to a user on collection element 8.

Figure 8:
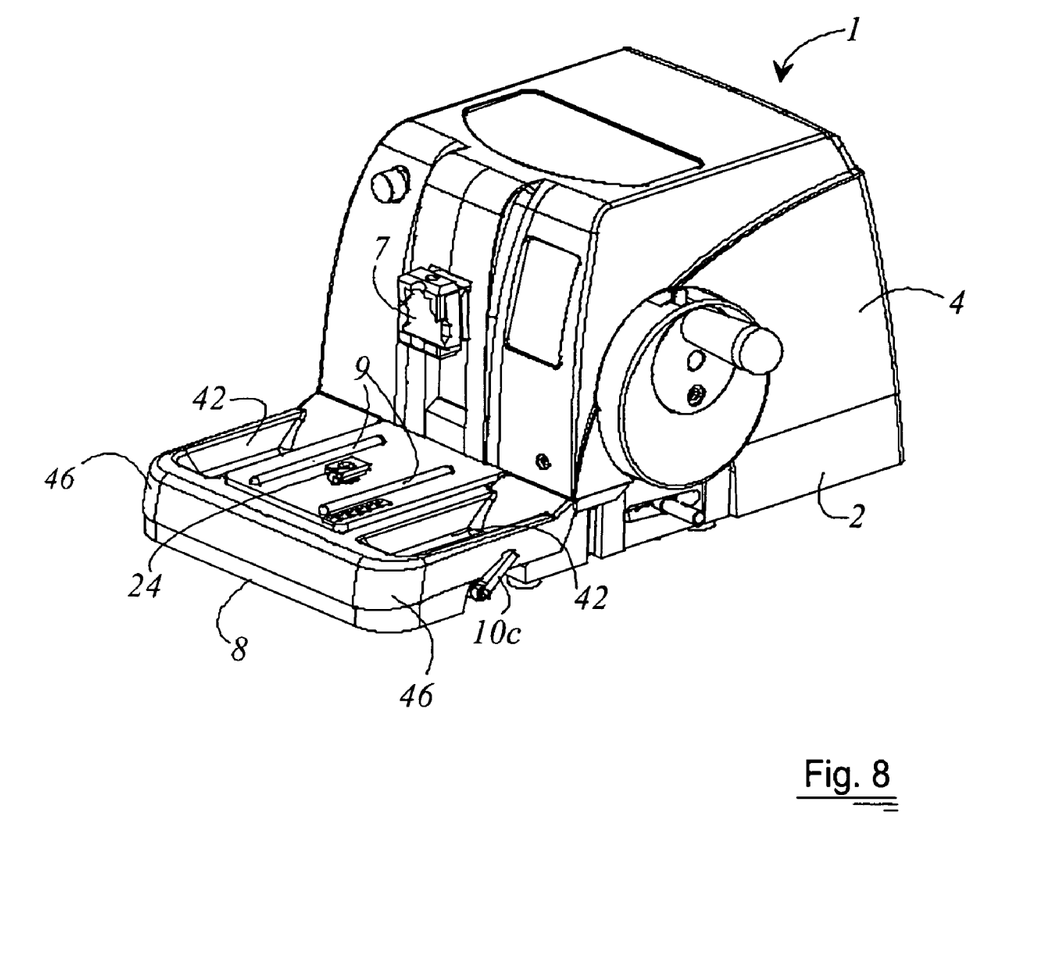
FIG. 8 is a perspective view of the rotary microtome with a collection element arranged on the microtome housing, in a further embodiment.

FIG. 8 shows rotary microtome 1 in a perspective view, joined to a further embodiment of collection element 8. For simplicity's sake, identical reference characters are used for elements identical to those in FIG. 1. Rotary microtome 1 substantially comprises a base part 2 and a microtome housing 4 provided on the base part. A knife holder 6 (omitted here) is placed on base part 2. Provided on base part 2 are two rail elements 9 on which knife holder can be modified in terms of its distance with respect to sample holder 7. Knife holder 6 is surrounded by a collection element 8. Collection element 8 possesses a respective depression 42 to the left and to the right of the knife holder, and adjoins microtome housing 4 and base part 2 without a step. At least one clamping lever 10c is provided on a side wall of collection element 8 and coacts via a mechanical coupling 24 with knife holder 6. By means of this clamping lever 10c, knife holder 6 is clamped with respect to base part 2.

Figure 9:
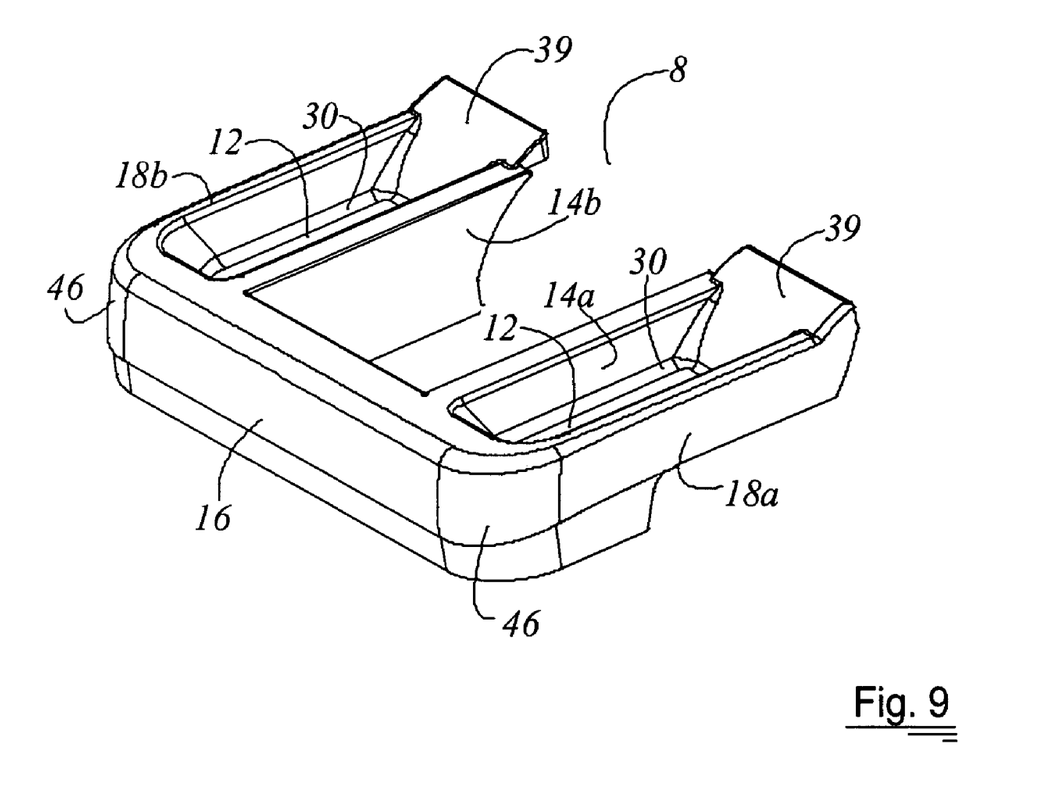
FIG. 9 is a perspective view of the collection element in the embodiment associated with the microtome housing in FIG. 8.

FIG. 9 is a perspective depiction of collection element 8, in the embodiment associated with microtome housing 4 in FIG. 8. Collection element 8 has embodied in it two depressions 42 that are arranged to the left and to the right of knife holder 6 when collection element 8 is joined to the microtome. In this embodiment, collection element 8 is constituted substantially from a first inner side wall 14a, a front wall 16, and a second inner side wall 14b, which are joined via a bottom 12 respectively to an outer side wall 18a and an outer side wall 18b. Bottom 12 continues, at the side located opposite front wall 16, into a respective contour surface 39 that adapts to a corresponding configuration of base part 2. The transition between bottom 12 and outer side wall 18b or outer side wall 18a or front wall 16 is equipped with a fillet 30. A fillet 30 is likewise embodied at the transition between first inner side wall 14a or second inner side wall 14b and bottom 12. Mechanical coupling 24 from clamping lever 10c to knife holder 6 is guided under bottom 12 of collection element 8. In an embodiment, bottom 12 has an elevation 22 under which, as already described in FIG. 5, mechanical coupling 24 is guided. Collection element 8 is equipped with fillets 30 at all corners and edges. This has the critical advantage that deposits of sample fragments cannot form in either corners or edges. A configuration of collection element 8 with fillets 30 furthermore greatly facilitates cleaning.

What is claimed is:

1. A rotary microtome comprising:
   a base part on which a microtome housing and a knife holder is arranged;
   a collection element which surrounds the knife holder on three sides, wherein the collection element is defined by a bottom, a first and a second inner side walls, a front wall, and a first and a second outer side walls;
   several clamping levers are coupled with the knife holder; wherein at least one clamping lever for the knife holder is arranged operably on the first or second outer side wall; and
   a mechanical coupling is guided under the bottom of the collection element from the clamping lever to the knife holder.

2. The rotary microtome as defined in claim 1, said front wall comprises an outer front wall and wherein the collection element is a pan having a U-shaped base outline; and the first and the second outer side walls are joined to one another by said outer front wall so that the pan surrounds the knife holder on three sides.

3. The rotary microtome as defined in claim 2, said front wall further comprises an inner front wall and wherein the first and the second inner side walls, the first and the second outer side walls, the inner front wall, and the outer front wall abut together with the bottom of the collection element in a fillet.

4. The rotary microtome as defined in claim 2, wherein the first outer side wall, the second outer side wall, and the outer front wall are dimensioned in such a way that the first outer side wall and the second outer side wall have a lesser spacing at the outer front wall than at the base part.

5. The rotary microtome as defined in claim 1, wherein the bottom of the collection element has shaped on it an elevation under which the mechanical coupling is guided from the at least one clamping lever to the knife holder.

6. The rotary microtome as defined in claim 1, wherein the knife holder is equipped with a hex socket screw which makes possible unrestricted angular adjustment of a knife support element and thus of a knife provided on the knife support element.

7. The rotary microtome as defined in claim 1, wherein a first clamping lever serves to immobilize a knife carriage on a knife support element; and a second clamping lever serves to clamp a knife.

8. The rotary microtome as defined in claim 1, wherein the first and the second outer side walls adjoin the microtome housing in such a way that no step is formed in the region where the first and the second outer side wall encounter the microtome housing.

9. The rotary microtome as defined in claim 1, wherein the collection element is embodied in one piece.

10. The rotary microtome as defined in claim 9, wherein the collection element comprises a magnetizable element that coacts with at least one magnet that is provided correspondingly on the base part of the rotary microtome.

11. The rotary microtome as defined in claim 1, said front wall comprises an inner front wall and wherein the base part has a peripheral step configured beneath the knife holder, and the first and the second inner side walls and the inner front wall adjoin the base part in such a way that the peripheral step projects beyond the first and the second inner side walls and the front wall.

12. The rotary microtome as defined in claim 1, wherein the first and the second inner side walls, the first and the second outer side walls, and the front wall abut together with the bottom of the collection element in a fillet.

13. The rotary microtome as defined in claim 1, wherein the first outer side wall, the second outer side wall, and the front wall are respectively joined to one another via a fillet.

14. A device for a rotary microtome comprising:
    a knife holder surrounded on three sides by a collection element, said collection element comprises a bottom, a first and a second inner side walls, and a front wall, as well as a first and a second outer side walls; and
    a mechanical coupling is guided under the bottom of the collection element, wherein the mechanical coupling provides a mechanical connection from at least one clamping lever, arranged on the first or second outer side wall, to the knife holder.

15. The device as defined in claim 14, said front wall comprises an outer front wall and wherein the collection element is a pan having a U-shaped base outline; and the first and the second outer side walls are joined to one another by said outer front wall so that the pan encloses the knife holder on three sides.

16. The device as defined in claim 15, said front wall further comprises an inner front wall and wherein the first and the second inner side walls, the first and the second outer side walls, the inner front wall, and the outer front wall abut together with the bottom of the collection element in a fillet.

17. The device as defined in claim 15, wherein the first outer side wall, the second outer side wall, and the outer front wall are respectively joined to one another via a fillet.

18. The device as defined in claim 17, wherein the first outer side wall, the second outer side wall, and the outer front wall are dimensioned in such a way that the first outer side wall and the second outer side wall have a lesser spacing at the outer front wall than at the base part.

19. The device as defined in claim 14, wherein the bottom of the collection element has shaped on it an elevation under which the mechanical coupling is guided from the at least one clamping lever to the knife holder.

20. The device as defined in claim 14, wherein the collection element is embodied in one piece.

21. The device as defined in claim 20, wherein the collection element is manufactured of plastic.

22. The device as defined in claim 14, wherein the first and the second inner side walls, the first and the second outer side walls, and the front wall abut together with the bottom of the collection element in a fillet.

23. The device as defined in claim 14, wherein the first outer side wall, the second outer side wall, and the front wall are respectively joined to one another via a fillet.

24. A rotary microtome comprising:
    a base part on which a microtome housing and a knife holder is arranged;
    a collection element which surrounds the knife holder on three sides, wherein the collection element is defined by a bottom, a first and a second inner side wall, an inner front wall and an outer front wall, and a first and a second outer side wall;
    several clamping levers are coupled with the knife holder; wherein at least one clamping lever for the knife holder is arranged operably on the first or second outer side wall; and
    a mechanical coupling is guided under the bottom of the collection element from the clamping lever to the knife holder.

25. A device for a rotary microtome comprising:
    a knife holder surrounded on three sides by a collection element, said collection element comprises a bottom, a first and a second inner side walls, an inner front wall and an outer front wall, as well as a first and a second outer side walls; and a mechanical coupling is guided under the bottom of the collection element, wherein the mechanical coupling provides a mechanical connection from at least one clamping lever, arranged on the first or second outer side wall, to the knife holder.

* * * * *